United States Patent
Mori et al.

(10) Patent No.: US 10,595,789 B2
(45) Date of Patent: Mar. 24, 2020

(54) MEAL TIME ESTIMATION METHOD, MEAL TIME ESTIMATION DEVICE, AND RECORDING MEDIUM

(71) Applicant: FUJITSU LIMITED, Kawasaki-shi, Kanagawa (JP)

(72) Inventors: Tatsuya Mori, Isehara (JP); Akihiro Inomata, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 84 days.

(21) Appl. No.: 15/693,967

(22) Filed: Sep. 1, 2017

(65) Prior Publication Data

US 2017/0360380 A1 Dec. 21, 2017

Related U.S. Application Data

(63) Continuation of application No. PCT/JP2015/057041, filed on Mar. 10, 2015.

(51) Int. Cl.
| | |
|---|---|
| A61B 5/00 | (2006.01) |
| A61B 5/0245 | (2006.01) |
| G09B 19/00 | (2006.01) |
| G16H 50/30 | (2018.01) |
| G16H 40/63 | (2018.01) |
| G16H 20/60 | (2018.01) |
| A61B 5/024 | (2006.01) |
| G09B 5/06 | (2006.01) |

(52) U.S. Cl.
CPC .......... *A61B 5/7275* (2013.01); *A61B 5/0245* (2013.01); *A61B 5/02438* (2013.01); *G09B 5/06* (2013.01); *G09B 19/0092* (2013.01); *G16H 20/60* (2018.01); *G16H 40/63* (2018.01); *G16H 50/30* (2018.01); *A61B 5/7239* (2013.01); *A61B 2562/0219* (2013.01)

(58) Field of Classification Search
CPC .. A61B 5/7275; A61B 5/0245; G09B 19/0092
See application file for complete search history.

(56) References Cited

U.S. PATENT DOCUMENTS

| | | |
|---|---|---|
| 5,398,688 A | 3/1995 | Laniado |
| 2006/0094938 A1 | 5/2006 | Shimada et al. |
| (Continued) | | |

FOREIGN PATENT DOCUMENTS

| | | |
|---|---|---|
| JP | 10-504739 | 5/1998 |
| JP | 2003-173375 | 6/2003 |
| (Continued) | | |

OTHER PUBLICATIONS

Extended European Search Report dated Feb. 22, 2018 in corresponding European Application No. 15884566.9.

(Continued)

*Primary Examiner* — William J Levicky
(74) *Attorney, Agent, or Firm* — Staas & Halsey, LLP

(57) ABSTRACT

A meal time estimation method includes: acquiring time series data of heart rate, by a processor; calculating a feature amount obtained by indexing a degree of similarity with a feature of heart rate change that appears at end of a meal from the time series data of the heart rate, by the processor; and estimating a meal time from the feature amount, by the processor.

7 Claims, 8 Drawing Sheets

(56) References Cited

U.S. PATENT DOCUMENTS

| | | | | |
|---|---|---|---|---|
| 2012/0172792 A1* | 7/2012 | Baynham | ............ | A61B 5/0245 |
| | | | | 607/62 |
| 2014/0275748 A1* | 9/2014 | Dunki-Jacobs | ...... | A61B 5/0537 |
| | | | | 607/62 |
| 2014/0275854 A1 | 9/2014 | Venkatraman et al. | | |

FOREIGN PATENT DOCUMENTS

| | | |
|---|---|---|
| JP | 2004-81471 | 3/2004 |
| JP | 2006-129887 | 5/2006 |
| JP | 2007-48180 | 2/2007 |
| JP | 2008-61790 | 3/2008 |
| JP | 2011-4968 | 1/2011 |
| JP | 2011-115508 | 6/2011 |
| WO | WO 2008/001366 A2 | 1/2008 |

OTHER PUBLICATIONS

Itao et al., "HealthCare Monitoring System Design and Applications in Cloud Computing Era", CMC Publishing Co.,Ltd., Sep. 3, 2012, pp. 297-298.

Sato et al.,"Seitai Data to Kasokudo Data o Mochiita Kodo Ninshiki", Dai 65 kai(Heisei 15 Nen) Zenkoku Taikai Koen Ronbunshu(5), Information Processing Society of Japan, Mar. 25, 2003, pp. 5-239-5-242.

International Search Report dated May 19, 2015 in corresponding International Application No. PCT/JP2015/057041.

Written Opinion of International Search Authority dated May 19, 2015 in corresponding International Application No. PCT/JP2015/057041.

\* cited by examiner

MEAL TIME ESTIMATION METHOD, MEAL TIME ESTIMATION DEVICE, AND RECORDING MEDIUM

CROSS-REFERENCE TO RELATED APPLICATION

This application is a continuation application of International Application PCT/JP2015/057041, filed on Mar. 10, 2015, and designating the U.S., the entire contents of which are incorporated herein by reference.

FIELD

The present invention relates to a meal time estimation method, a meal time estimation program, and a meal time estimation device.

BACKGROUND

Health care such as prevention of life-style related diseases including metabolic syndrome and diabetes, diet, and medical services is attracting attention. When such health care is performed, process of finding a problem of own lifestyle habits and improving the problem, by recording lifestyle habits such as daily exercise and meals, is needed.

For example, as a preventive measure related to the "meal", a control method of the meal for "when", "what", and "how many" is mentioned as follows. Particularly, items such as having three meals regularly (when), having breakfast (when), taking a balanced nutrition (what), not having too much calories (how many), and cutting down on salt (what), are mentioned.

For example, when there is a record of "when" a user ate, a service of detecting irregular eating habits and providing preventive advice can be performed.

For example, as an example of a technique of performing meal determination, an eating behavior detecting system, an utterance/eating and drinking condition detecting system, and an eating behavior detecting device are suggested. For example, in the eating behavior detecting system, the meal determination is performed by detecting a movement of lifting an arm up and down when eating food, by using an acceleration sensor. In addition, in the utterance/eating and drinking condition detecting system, mastication when eating food is utilized to detect a frequency pattern of body sound that is unique to mastication. In addition, in case of the eating behavior detecting device, in a situation where an infrared sensor is installed on a table, or the like, threshold processing is performed for whether a human body frequently moves after the human body is detected near the table.

However, any of these techniques has limitation in a way of meal or limitation of a place where the eating behavior is estimated, for estimating the eating behavior. Thus, they lack versatility in a way. For example, a tendency of acceleration estimated by the eating behavior detecting system only corresponds to one side of arm movement performed when eating food. When the other arm movement is performed, the tendency of acceleration is different. Therefore, detection failure occurs. In addition, in a case of the utterance/eating and drinking condition detecting system, a microphone is mounted around the neck during the meal time. This applies a burden to the body and makes one's appearance look bad. In addition, in the eating behavior detecting device, only meals in a fixed environment such as a place where the infrared sensor is installed, can be recognized.

In addition, as an example of techniques using pulse waves for the meal determination, a life management terminal device is also suggested. In this life management terminal device, it is determined that the user is having a meal when, in addition to the appearance of mastication characteristics generated during a meal time, the pulse rate increases, and there is no sharp rise in the skin conductance rate.

Patent Document 1: Japanese Laid-open Patent Publication No. 2011-4968

Patent Document 2: Japanese Laid-open Patent Publication No. 2003-173375

Patent Document 3: Japanese Laid-open Patent Publication No. 2011-115508

Patent Document 4: Japanese Laid-open Patent Publication No. 2004-81471

Patent Document 5: Japanese Laid-open Patent Publication No. 2008-61790

Patent Document 6: Japanese National Publication of International Patent Application No. 10-504739

Patent Document 7: Japanese Laid-open Patent Publication No. 2006-129887

SUMMARY

According to an aspect of the embodiments, a meal time estimation method includes: acquiring time series data of heart rate, by a processor; calculating a feature amount obtained by indexing a degree of similarity with a feature of heart rate change that appears at end of a meal from the time series data of the heart rate, by the processor; and estimating a meal time from the feature amount, by the processor.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS in the techniques described above, sometimes erroneous determination occurs for the meal time as described below.

That is, in the life management terminal device described above, the skin conductance rate is used for the meal determination. Measurement accuracy of the skin conductance rate decreases in the case of sweating or the like. Thus, the possibility that erroneous determination occurs in the meal determination increases. In addition, even when the skin conductance rate is not used and only the pulse rate is used in the life management terminal device described above, the pulse rate increases by a factor other than the meal, such as mental tension, change in environmental temperature, and exercises. Thus, erroneous determination occurs also in this case.

In one aspect, the disclosed embodiments have an object of providing a meal time estimation method, a meal time estimation program, and a meal time estimation device that can prevent a decrease in measurement accuracy of a meal time.

A meal time estimation method, a meal time estimation program, and a meal time estimation device according to the present application will be described in detail below with reference to the accompanying drawings. Note that the embodiments are not limited to the disclosed technique. The embodiments can be combined as appropriate as long as the processing contents do not contradict each other.

First Embodiment

[System Configuration]

Figure 1:
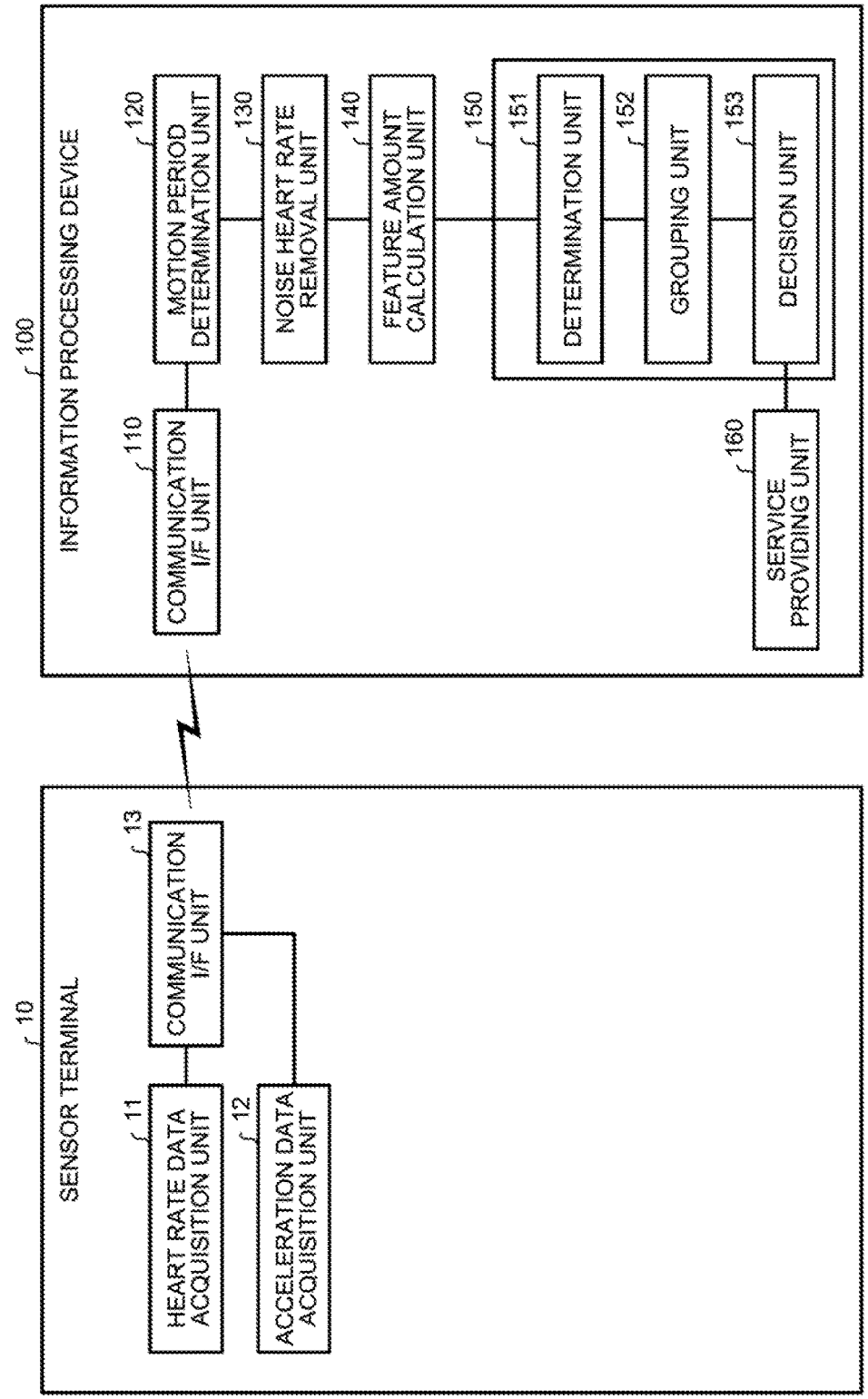
FIG. 1 is a diagram illustrating a configuration of a health care supporting system according to a first embodiment.

FIG. 1 is a diagram illustrating a configuration of a health care supporting system according to a first embodiment. A health care supporting system 1 illustrated in FIG. 1 provides various types of health care supporting services. For example, examples of the health care supporting services include a service of recording daily activities such as a meal time, of a user of a sensor terminal 10 by using sensing data collected by the sensor terminal 10, and further, a derivative service of utilizing the record.

As part of such health care supporting services, the health care supporting system 1 uses a feature amount obtained by indexing a degree of similarity with a feature of heart rate change that appears at the end of a meal, when estimating a meal time such as a meal start time, a meal end time, and a duration time for a meal from the time series data of the heart rate. This prevents the meal time from being estimated in a situation where the heart rate increases due to a factor other than the meal such as mental tension, change in environmental temperature, and exercises, and thereby prevents a decrease in the estimation accuracy of the meal time.

As illustrated in FIG. 1, the health care supporting system 1 accommodates the sensor terminal 10, and an information processing device 100. Note that, although FIG. 1 illustrates a case of one sensor terminal, the health care supporting system 1 may accommodate a plurality of sensor terminals.

The sensor terminal 10 and the information processing device 100 are mutually communicatively connected. As an example, a case where the sensor terminal 10 and the information processing device 100 are connected by short range wireless communication such as Bluetooth (trademark) Low Energy (BLE), is assumed. However, they can be connected via any network regardless of wired or wireless connection. For example, the sensor terminal 10 and the information processing device 100 can be connected via any type of communication network such as local area networks such as a local area network (LAN), a virtual private network (VPN), and the Internet.

The sensor terminal 10 is a terminal device mounted with a sensor.

As an embodiment, for the sensor terminal 10, a terminal device dedicated for health care, a wearable gadget such as smart glasses and a smart watch, and the like can be adopted.

The sensor terminal 10 is mounted with, at least a heart rate sensor. By using this heart rate sensor, the sensor terminal 10, for example, detects the heart rate per unit time of the user that utilizes the sensor terminal 10. The time series data of the heart rate sensed by using the heart rate sensor in this way is used for calculating the feature amount and estimating the meal time. Hereinafter, the time series data of the heart rate sensed by using the heart rate sensor is sometimes described as "heart rate data". The sensor terminal 10 can be mounted with an acceleration sensor besides the heart rate sensor. As an example, for the acceleration sensor, a three-axis acceleration sensor can be adopted. The time series data of the three-axis acceleration sensed by using the acceleration sensor in this way, that is, vertically, horizontally or longitudinally acceleration change of the sensor terminal 10 is used by the user that uses the sensor terminal 10 for detecting a motion state such as walking, going up and down, and running. Thus, the time series data of the acceleration contributes to removal of the moving state and a motion period in which the motion state continues from the time series data of the heart rate. Hereinafter, the time series data of the acceleration sensed by using the acceleration sensor is sometimes described as "acceleration data". Note that, although the heart rate sensor and the acceleration sensor are exemplified, other sensors such as a gyro sensor and the Global Positioning System (GPS) receiver may be mounted. For example, the gyro sensor can be used instead of the acceleration sensor. In this way, the sensor for removing the motion period is not limited to the acceleration sensor. The motion period can be removed from the heart rate data by using inertial data sensed by an inertial sensor.

When the sensor terminal 10 is mounted with the heart rate sensor, a wearable heart rate sensor that is mounted to a body part of the user such as a chest, an arm, and a wrist can be adopted. For example, a pulse by a photoplethysmography sensor can be adopted. In this case, the heart rate sensor can be mounted only for the health care, or, when the wearable gadget is mounted with the heart rate sensor, the heart rate sensor can also be used. Furthermore, the heart rate sensor that detects the heart rate is not necessarily mounted to the sensor terminal 10 and an electrocardiogram sensor that detects an electrocardiogram signal may be mounted to the sensor terminal 10. In addition, for the heart rate sensor, a wearable one is not adopted necessarily. For example, detection of the heart rate may be implemented in a state of not contacting with the body part of the user by detecting the heart rate from the time series change of brightness related to an image of a part of the living body of the user imaged with a predetermined sampling frequency, or detecting a Doppler frequency accompanied with heartbeat by using a radio frequency (RF) motion sensor.

The heart rate is an index that represents the heart beat rate of the heart that pumps blood out. A calculation method of the heart rate may be a method of measuring an electrical activity of the heart, or a method of measuring a pulse by measuring a blood flow.

The heart rate data and the acceleration data that have been sensed by the sensor terminal 10 in this way are transmitted to the information processing device 100 in a state of being associated with identification information of the user, for example a machine name and a serial number of the sensor terminal 10. At this time, the heart rate data and the acceleration data may be transmitted in real time each time the heart rate or the acceleration is sensed, or may be transmitted after the data is accumulated for a predetermined period, for example, 12 hours, a day, a week, or a month. Note that although a case where the heart rate data and the acceleration data are transmitted from the sensor terminal 10 to the information processing device 100 is exemplified, the sensor terminal 10 may calculate the feature amount used for estimating the meal time from the heart rate data. When the feature amount is calculated by the sensor terminal 10 in this way, a data amount transmitted by two devices can be reduced and a situation where the heart rate data that is personal information can be prevented from being disclosed to a third person, in transmission.

The information processing device 100 is a computer that provides the health care supporting service described above. For the information processing device 100, a general computer such as a mobile terminal device, and a desktop or laptop personal computer can be adopted. Note that the category of the mobile terminal device described above includes not only a mobile communication terminal such as a smartphone, a mobile phone and a Personal Handyphone System (PHS) but also a tablet terminal and a slate terminal.

As an embodiment, the information processing device 100 can be mounted by installing a meal time estimation program that implements the health care supporting service described above as package software or online software, in a desired computer. For example, the information processing device 100 estimates the meal time of the user of the sensor terminal 10 by using the heart rate data received from the sensor terminal 10. Thus, the information processing device 100 can record the meal time, and in addition, can generate a list of a meal time zone for a predetermined period, for example, a week, from the meal time recorded by that time and output the list, and can analyze for eating habits or diet from the meal time recorded by that time and output various types of advice. For example, the information processing device 100 can output various types of advice described above through an output device such as a display device, a speech output device, and a printing device that are included in the information processing device 100. In addition, an output destination of the information is not necessarily limited to the information processing device 100. The destination may be other terminal devices that the user uses, or a terminal device that a related person such as a relative of the user, and a person in charge of medical or nursing care uses. Thus, the health care supporting service described above is implemented.

[Configuration of Sensor Terminal 10]

Next, a functional configuration of the sensor terminal 10 according to the present embodiment will be described. As illustrated in FIG. 1, the sensor terminal 10 has a heart rate data acquisition unit 11, an acceleration data acquisition unit 12, and a communication interface (I/F) unit 13. Note that the sensor terminal 10 may have a function unit that a known computer has, other than a function unit illustrated in FIG. 1. For example, when the terminal device only for the health care, the wearable gadget, or the mobile terminal device is performed as the sensor terminal 10, hardware and software that each of these devices includes as standard equipment can be mounted.

The heart rate data acquisition unit 11 is a processing unit that acquires the heart rate data described above.

As an embodiment, the heart rate data acquisition unit 11 controls the heart rate sensor (not illustrated) to cause the heart rate sensor to sense the heart rate in a predetermined sampling period. Thus, the heart rate data acquisition unit 11 acquires the time series data of the heart rate sensed by the heart rate sensor for each sampling point as the heart rate data. As the heart rate data, as an example, data associated with items such as time and the heart rate can be adopted. The "time" described here may be system time managed locally on the sensor terminal 10, for example, elapsed time from any start time point, or may be time represented by a calendar representing a year, a month, a day, an hour, a minute, a second, and the like. The "heart rate" is represented as the heart rate per unit time. For example, when the unit time is a minute, the heart rate is represented by beats per minute (bpm) or the like. In addition, when the unit time is a second, the heart rate is represented by Hz. Furthermore, an index corresponding to the "heart rate" other than the heart rate itself may be used. For example, a peak RR interval of an electrocardiographic waveform in the electrocardiographic waveform is represented by millisecond and can be used instead of the heart rate.

The present invention acquires a response of a circulatory organ used when having a meal and used for estimating the meal time. When an index corresponding to the heart rate can be acquired from information acquired from the electrocardiographic waveform and the pulse wave waveform and information related to the blood flow rate, other than the heart rate, the index can be used.

The heart rate data acquired in this way may be transmitted to the information processing device 100 via the communication I/F unit 13 each time the heart rate is sensed, or may be transmitted to the information processing device 100 via the communication I/F unit 13 after the heart rate data is accumulated to a memory (not illustrated) for a predetermined period, for example, 12 hours, or a day.

The acceleration data acquisition unit 12 is a processing unit that acquires the acceleration data described above.

As an embodiment, the acceleration data acquisition unit 12 controls the acceleration sensor (not illustrated) to cause the acceleration sensor to sense the three-axis acceleration, that is, the vertical, horizontal or longitudinal acceleration, in a predetermined sampling period. Thereby, the acceleration data acquisition unit 12 acquires the time series data of the vertical, horizontal or longitudinal acceleration sensed by the acceleration sensor for each sampling point, as the acceleration data. For the acceleration data, as an example, data associated with items such as time and acceleration can be adopted. The "time" described here may be system time managed locally on the sensor terminal 10, for example, the elapsed time from any start time point, or may be time represented by a calendar representing a year, a month, a day, an hour, a minute, a second, and the like, as similar to the heart rate data described above. In addition, the "acceleration" can include the vertical, horizontal or longitudinal three-axis acceleration. For example, when the acceleration of a part of direction of the three-axis acceleration is used by a function unit at a later stage, the acceleration of the direction not used by the function unit at a later stage can be removed from the acceleration data. Note that, for the acceleration sensor, the same sampling period as the heart rate sensor can be adopted and a different sampling period can be adopted.

The acceleration data acquired in this way may be transmitted to the information processing device 100 via the communication I/F unit 13 each time the acceleration is sensed, or may be transmitted to the information processing device 100 via the communication I/F unit 13 after the heart rate data is accumulated to a memory (not illustrated) for a predetermined period, for example, 12 hours, or a day.

The communication I/F unit 13 is an interface that performs communication control between the other devices, for example, the information processing devices 100.

As an embodiment, for the communication I/F unit 13, a network interface card such as a LAN card can be adopted. For example, the communication I/F unit 13 transmits the heart rate data described above, the acceleration data described above, and the like to the information processing device 100. In addition, the communication I/F unit 13 can receive an instruction of uploading the heart rate data described above and the acceleration data described above from the information processing device 100 to the information processing device 100, an instruction for an interval of uploading the data to the information processing device 100, and in addition to that, an estimation result of the meal time, a diagnosis result using the estimation result, and the like.

Note that the function units such as the heart rate data acquisition unit 11 and the acceleration data acquisition unit 12 described above can be mounted as follows. For example, the function units can be implemented by causing, for example, a central processing unit, what is called a CPU, to expand process that exhibits the similar function to the heart rate data acquisition unit 11 and the acceleration data acquisition unit 12 described above, on the memory and execute the process. These function units are not necessarily performed in the central processing unit, and may be performed by a micro processing unit (MPU). In addition, each of the function units described above can be implemented also by a hardwired logic such as an application specific integrated circuit (ASIC) and a field programmable gate array (FPGA).

In addition, for a main storage device used by each of the function units described above, as an example, various types of semiconductor memory elements, for example, a random access memory (RAM), or a flash memory can be adopted. In addition, the storage device referred to by each of the function units described above is not necessarily the main storage device, and may be an auxiliary storage device. In this case, a hard disc drive (HDD), an optical disc, a solid state drive (SSD), or the like can be adopted.

[Configuration of Information Processing Device 100]

Next, functional configuration of the information processing device 100 according to the present embodiment will be described. As illustrated in FIG. 1, the information processing device 100 includes a communication I/F unit 110, a motion period determination unit 120, a noise heart rate removal unit 130, a feature amount calculation unit 140, a meal time estimation unit 150, and a service providing unit 160. Note that the information processing device 100 may have a function unit that a known computer has, other than the function units illustrated in FIG. 1, for example, various types of input and output devices.

The communication I/F unit 110 is an interface that performs communication control between other devices, for example, the sensor terminals 10.

As an embodiment, for the communication I/F unit 110, a network interface card such as a LAN card can be adopted.

For example, the communication I/F unit 110 receives the heart rate data described above, the acceleration data described above, and the like from the sensor terminal 10. In addition, the communication I/F unit 110 can transmit an instruction of uploading the heart rate data described above and the acceleration data described above to the sensor terminal 10, an instruction for an interval of uploading the data to the information processing device 100, and in addition to that, an estimation result of the meal time, a diagnosis result using the estimation result, and the like, to the sensor terminal 10.

The motion period determination unit 120 is a processing unit that determines the motion period. The "motion period" described here refers to a period in which motion such as walking, running, and stepping the stairs is estimated to be performed. For example, for the determination of the motion period, the acceleration data transmitted from the sensor terminal 10 is used.

As an embodiment, the motion period determination unit 120 uses at least the vertical acceleration, that is, the acceleration of the direction of gravitational force, among the acceleration included in the acceleration data described above, for the determination of the motion period described above. The reason of that the acceleration of the direction of gravitational force is used as above is that, when the motion such as walking, running, and stepping the stairs is performed, the acceleration changes in a specific pattern and the pattern appears periodically. That is, at the time of the motion such as walking, running, and stepping the stairs, a reaction force is applied from a ground, or the like at the time of kicking out and landing of a leg part, and thereby change of increasing and decreasing of the acceleration of the direction of gravitational force appears in a short period. Furthermore, the change of increasing and decreasing of the acceleration of the direction of gravitational force appears periodically each time a load is off from the ground and a foot lands on the ground.

Thus, the motion period determination unit 120 detects a pattern of the increasing and decreasing described above from the acceleration of the direction of gravitational force, as an example. In addition, the motion period determination unit 120 determines whether the interval of the appearance of the pattern is within a predetermined period. At this time, when the interval of the appearance of the pattern is within the predetermined period, the motion period determination unit 120 determines that a section in which the pattern appears repeatedly in the predetermined period is the motion period. As an example, in the determination of the motion period, the user performs motion behavior in a state of being mounted with the sensor terminal 10, the acceleration change with the motion behavior is collected experimentally, and thereby, a threshold that distinguishes the increasing and the decreasing from an extent of the increasing and the decreasing that form the pattern described above, can be set. Furthermore, also for the interval of the appearance of the pattern, the predetermined period described above can be determined from a value that appears experimentally. Note that the motion period described above can be represented by a start time of the motion period and its duration, and can be represented as a motion start time and a motion end time. Note that also the motion period in which motion of an arm, a leg, an upper half body, a lower half body, a posture change, and the like that affect the heart rate change, can be regarded as the motion period described above.

The noise heart rate removal unit 130 is a processing unit that removes a section in which the heart rate is estimated to change due to a noise other than the meal from the heart rate data described above.

As an embodiment, the noise heart rate removal unit 130 removes a section that corresponds to the motion period determined by the motion period determination unit 120 in the heart rate data acquired by the heart rate data acquisition unit 11 in order to prevent the change of the heart rate with the motion from adversely affecting the estimation of the meal time.

At this time, the noise heart rate removal unit 130 can determine not only the section that corresponds to the motion period, but also, as an example, a removal period that includes a recovery change of the heart rate after motion by adding a certain period from the motion end time to the recovery of the heart rate increased due to the motion, and remove a section that corresponds to the removal period from the heart rate data. For the certain period added to the motion end time, as an example, a user-specific time can be set by performing an experiment for measuring the recovery change after the motion, and an all-user common time can be set as a default value. Note that when data of the section that corresponds to the motion period or the removal period is removed from the heart rate data, data of a part that is lost by the removal can be interpolated by performing linear interpolation, polynomial interpolation, spline interpolation, or the like.

The feature amount calculation unit 140 is a processing unit that calculates a feature amount obtained by indexing the degree of similarity with a feature of the heart rate change that appears at the end of a meal from the heart rate data described above.

As an embodiment, the feature amount calculation unit 140, while shifting a candidate of the meal end time assumed to be the meal end time in the heart rate data described above, calculates the feature amount described above by using partial data around the candidate in the heart rate data described above for every candidate.

Figure 2:
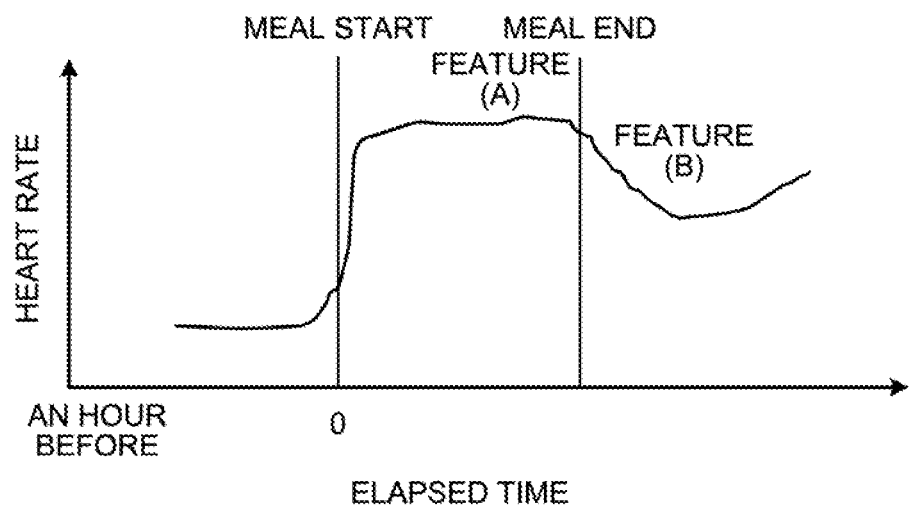
FIG. 2 is a diagram illustrating an example of heart rate data.
Figure 3:
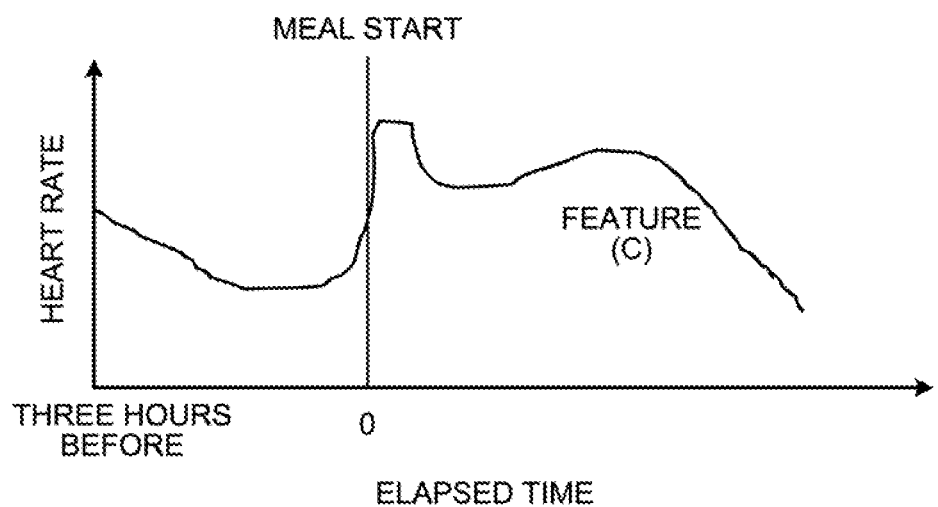
FIG. 3 is a diagram illustrating an example of the heart rate data.

Now, a feature of the heart rate change that appears at the end of a meal is described with reference to FIG. 2 and FIG. 3. FIG. 2 and FIG. 3 are diagrams illustrating an example of the heart rate data. These FIG. 2 and FIG. 3 illustrate the heart rate data including a meal period from the meal start to the meal end. Timing of the meal start and the meal end in the figures is time indicated as a reference by an input by the user. Among the figures, FIG. 2 illustrates the heart rate data from an hour before the meal start to an hour after the meal end. On the other hand, FIG. 3 illustrates the heart rate data of five hours before and after the meal start. In other words, FIG. 2 illustrates the heart rate data in a narrower view than that in FIG. 3, and FIG. 3 illustrates the heart rate data in a broader view than that in FIG. 2. Note that the vertical axis illustrated in FIG. 2 and FIG. 3 indicates the heart rate per unit time, and the horizontal axis indicates time.

According to the heart rate data illustrated in FIG. 2 and FIG. 3, a feature (a) and a feature (b) illustrated in FIG. 2 and a feature (c) illustrated in FIG. 3 appear at the end of a meal. That is, as illustrated in the feature amount (a) in FIG. 2, there is a tendency that a state in which the heart rate is high continues before the meal end time, for the reason that it is during the meal, as compared to before the meal. In addition, as illustrated in the feature (b) in FIG. 2, there is a tendency that the heart rate starts to decrease from the end of the meal. In addition, as illustrated in the feature (c) in FIG. 3, there is a tendency that the heart rate increases sometime after the end of a meal, probably due to digestion activity or the like in a body, and, for example, the heart rate that is higher than at the start of a meal is maintained for a long time of three to five hours.

According to these, by indexing the degree that the partial data around the candidate of the meal end time described above is similar with the feature (a), the feature (b), and the feature (c), as the feature amount, it can be evaluated whether the candidate is plausible as the meal end time.

For example, the feature amount calculation unit 140 can calculate seven feature amounts of a feature amount (1) to a feature amount (7) described below.

[Feature Amount (1)]

Figure 4:
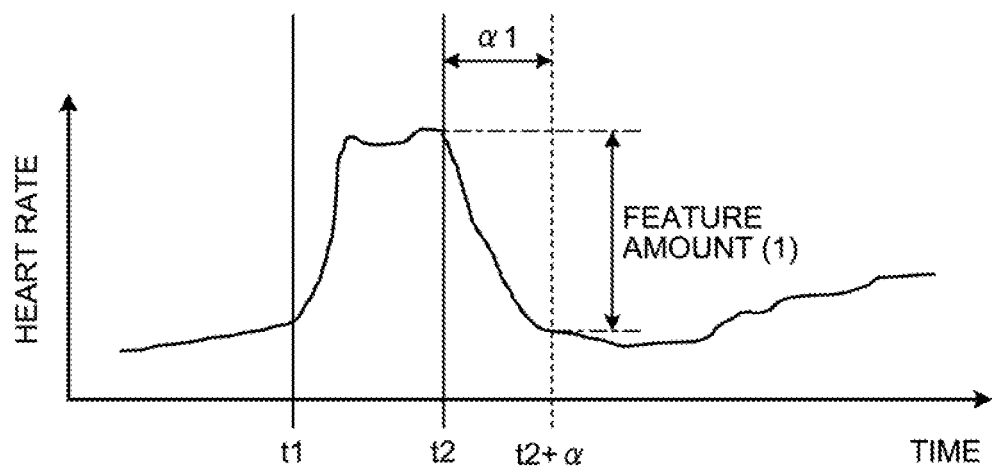
FIG. 4 is a diagram explaining an example of feature amount (1)

First, the feature amount (1) is described. The feature amount (1) is an index obtained by quantizing the extent of decrease of the heart rate after the end of a meal. FIG. 4 is a diagram explaining an example of the feature amount (1). FIG. 4 illustrates a case where the candidate of the meal end time described above is set at a time point input by the user as the meal end in the heart rate data including the actual meal period, for convenience of explanation. The vertical axis illustrated in FIG. 4 indicates the heart rate per unit time, and the horizontal axis indicates time. Note that "t1" illustrated in FIG. 4 indicates the meal start time and "t2" illustrated in FIG. 4 indicates the meal end time.

As illustrated in FIG. 4, the feature amount calculation unit 140, as an example, can calculate a difference between the heart rate measured at the meal end time t2 that is the candidate, and the heart rate after a predetermined time $\alpha 1$ from the meal end time t2, as the feature amount (1). As an example of the predetermined time $\alpha 1$, when the candidate is set to the actual meal end time, an extent of time, for example, an extent of time of three minutes or five minutes, or the like can be adopted in which the tendency of the feature (b) described above appears. In a case of the feature amount (1) calculated in this way, the relation among the feature amounts (1) calculated at rest time in which activities such as motion are not performed, at the actual meal end time, and at the end of motion is: at rest time<at the end of a meal<at the end of motion. Thus, as an example, it can be evaluated whether the candidate is plausible as the meal end time by setting an upper limit value of the feature amount (1) at the rest time and a lower limit value of the feature amount (1) at the end of motion, as boundary values obtained by experiments, pre-measuring, or the like, and by checking whether it satisfies: upper limit value at the rest time<feature amount (1)<lower limit value at the end of motion.

Note that, as an example, a case is described where the difference between the heart rate number measured at the meal end time t2 that is the candidate, and the heart rate after the predetermined time $\alpha 1$ from the meal end time t2, is determined as the feature amount (1). However, the calculation method of the feature amount (1) is not limited to this. As another example, the feature amount calculation unit 140 can calculate the heart rate that has the smallest value among the heart rates measured in a predetermined time from the meal end time t2, for example, 15 minutes or the like, as the feature amount (1).

[Feature Amount (2)]

Figure 5:
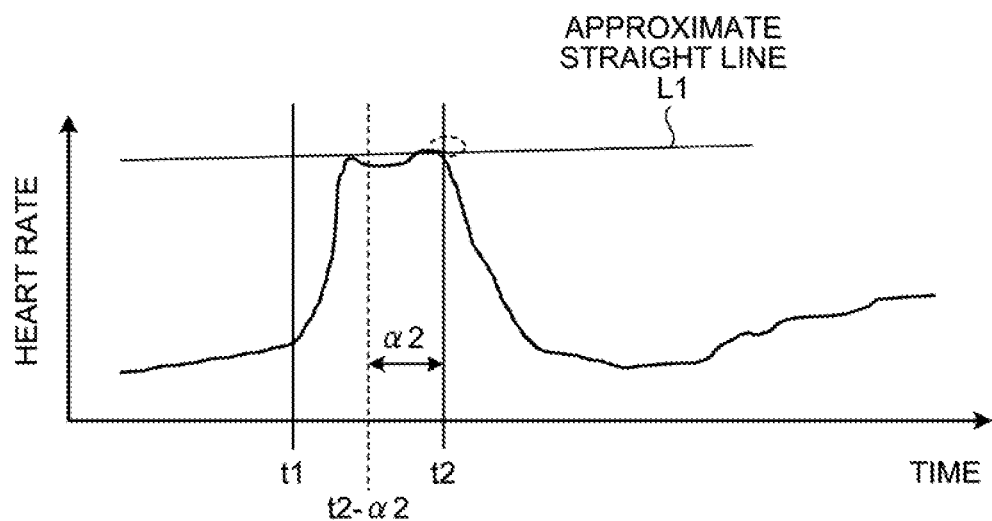
FIG. 5 is a diagram explaining an example of feature amount (2)

Next, the feature amount (2) will be described. The feature amount (2) is an index obtained by quantizing inclination of the heart rate immediately before the end of a meal, that is, inclination formed by the waveform of the heart rate data from during the meal to immediately before the end of a meal. FIG. 5 is a diagram explaining an example of the feature amount (2). FIG. 5 also illustrates, for convenience of explanation, a case where the candidate of the meal end time described above is set at a time point that the user inputs as the meal end in the heart rate data including the actual meal period. The vertical axis illustrated in FIG. 5 indicates the heart rate per unit time, and the horizontal axis indicates time. Note that "t1" illustrated in FIG. 5 indicates the meal start time and "t2" illustrated in FIG. 5 indicates the meal end time.

As illustrated in FIG. 5, the feature amount calculation unit 140, as an example, can calculate inclination of an approximate straight line L1 determined by performing function approximation by a linear function, or the like, on the time series of the heart rate included in the heart rate data in a section before predetermined time α2 from the meal end time t2 that is the candidate, as the feature amount (2). As an example of the predetermined time α2, an extent of time, for example, three minutes or the like can be adopted in which it is assumed that, when the user eats a certain amount of food, eating action and peristaltic action continue. It can be considered that as the value of the feature amount (2) calculated in this way comes close to zero, the heart rate during the meal shifts with an approximately stable value. Thus, it can be evaluated that the partial data around the candidate of the meal end time described above is similar to the feature (a).

[Feature Amount (3)]

Figure 6:
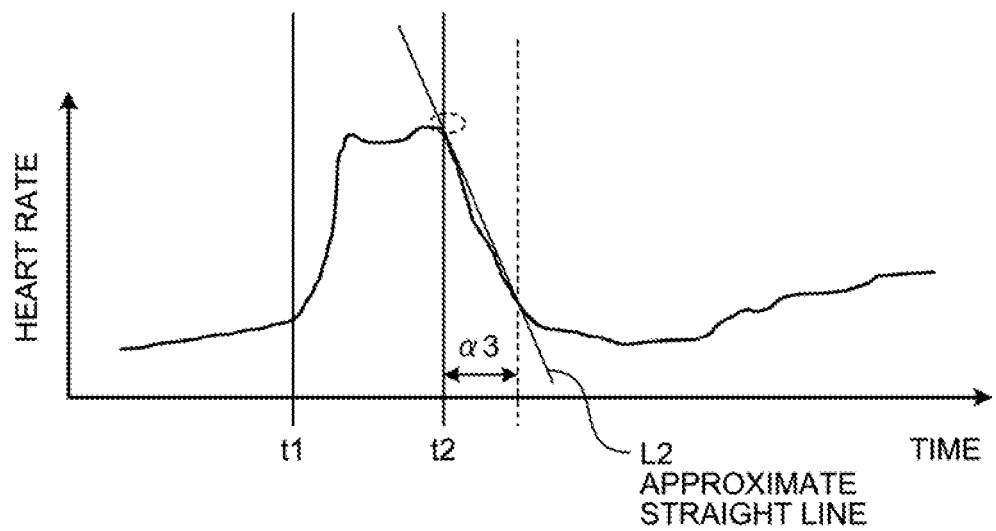
FIG. 6 is a diagram explaining an example of feature amount (3)

Next, the feature amount (3) will be described. The feature amount (3) is an index obtained by quantizing inclination of the heart rate immediately after the end of a meal, that is, inclination formed by the waveform of the heart rate data as the time elapses after the end of a meal. FIG. 6 is a diagram explaining an example of the feature amount (3). FIG. 6 also illustrates, for convenience of explanation, a case where the candidate of the meal end time described above is set at a time point that the user inputs as the meal end in the heart rate data including the actual meal period. The vertical axis illustrated in FIG. 6 indicates the heart rate per unit time, and the horizontal axis indicates time. Note that "t1" illustrated in FIG. 6 indicates the meal start time and "t2" illustrated in FIG. 6 indicates the meal end time.

As illustrated in FIG. 6, the feature amount calculation unit 140, as an example, can calculate inclination of an approximate straight line L2 determined by performing function approximation by a linear function, or the like, on the time series of the heart rate included in the heart rate data in a section until predetermined time α3 after the meal end time t2 that is the candidate, as the feature amount (3). As an example of the predetermined time α3, as similar to the α1 of the feature amount (1), an extent of time, for example, three minutes or five minutes, or the like can be adopted in which, when the candidate is set to the actual meal end time, the tendency of the feature (b) described above appears. In a case of the feature amount (3) calculated in this way, the relation among the feature amount (3) that can be calculated at the rest time in which activities such as motion are not performed, at the actual end of a meal and at the end of motion is: at the end of motion<at the end of a meal<at the rest time. Thus, as an example, it can be evaluated whether the candidate is plausible as the meal end time by setting an upper limit value of the feature amount (3) at the end of motion and a lower limit value of the feature amount (3) at the rest time, as boundary values and by checking whether it satisfies: upper limit value at the end of motion<feature amount (3)<lower limit value at the rest time.

Note that, a case is described where the function approximation is performed in the section until predetermined time α3 after the meal end time t2 that is the candidate, as an example of the calculation method of the feature amount (3). However, the calculation method of the feature amount (3) is not limited to this.

As another example, the feature amount calculation unit 140, when performing the function approximation by using the heart rate data after the meal end time t2 that is the candidate, performs the function approximation each time an end point of the section in which the function approximation is performed is shifted between a first time after the meal end time t2 and a second time after the meal end time t2, that is later than the first time. In addition, the feature amount calculation unit 140 can derive inclination of the approximate straight line that is the smallest among a plurality of approximate straight lines acquired by the function approximation, as the feature amount (3) as a result of the shift from the first time to the second time. In addition, the feature amount calculation unit 140 also can derive inclination of the approximate straight line having the smallest average error with the partial data of the heart rate data among the plurality of approximate straight lines acquired by the function approximation, as the feature amount (3) as a result of the shift from the first time to the second time. Note that, as an example of the first time described above, one minute can be adopted, and as an example of the second time described above, 10 minutes can be adopted. One factor that one minute can be adopted as an example of the first time is that enough data for having the tendency after the end of a meal can be acquired. In addition, one factor that 10 minutes can be adopted as an example of the second time is that the time includes enough features of after the end of a meal and other actions (for example, a nap) hardly affect the time.

[Feature Amount (4)]

Figure 7:
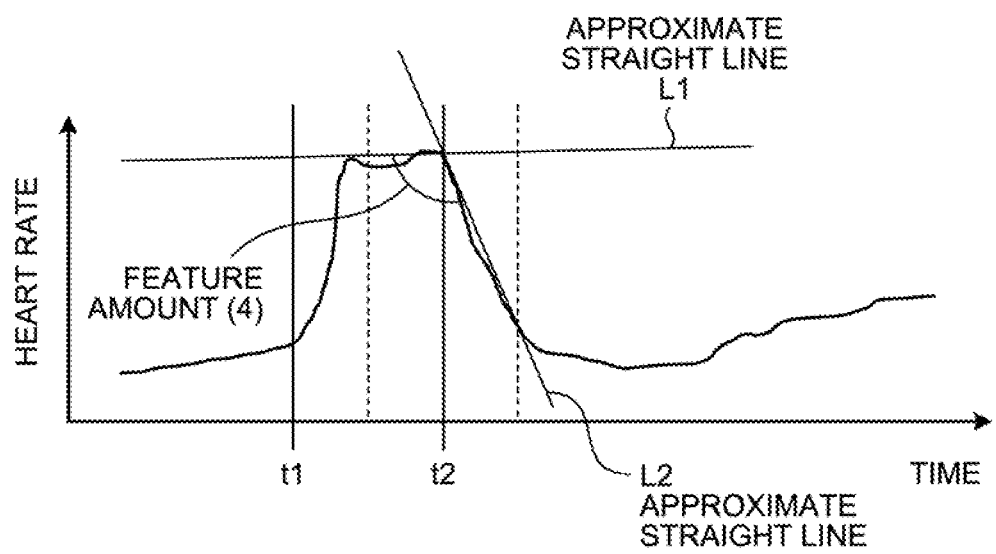
FIG. 7 is a diagram explaining an example of feature amount (4)

Next, the feature amount (4) will be described. The feature amount (4) is an index obtained by quantizing an angle between immediate before the end of a meal and immediately after the end of a meal, that is, an angle formed by the waveform of the heart rate data immediately before the end of a meal and immediately after the end of a meal. FIG. 7 is a diagram explaining an example of the feature amount (4). FIG. 7 also illustrates, for convenience of explanation, a case where the candidate of the meal end time described above is set at a time point that the user inputs as the meal end in the heart rate data including the actual meal period. The vertical axis illustrated in FIG. 7 indicates the heart rate per unit time, and the horizontal axis indicates time. Note that "t1" illustrated in FIG. 7 indicates the meal start time and "t2" illustrated in FIG. 7 indicates the meal end time.

As illustrated in FIG. 7, the feature amount calculation unit 140, as an example, can calculate an angle at which the approximate straight lines cross each other from the inclination of the approximate straight line L1 described above and the inclination of the approximate straight line L2 described above as the feature amount (4). In a case of the feature amount (4) calculated in this way, the relation among the feature amounts (1) that can be calculated at the rest time in which activities such as motion are not performed, at the actual meal end time, and at the motion end time is as follows. That is, the feature amount (4) that can be calculated at the end of motion tends to come close to approximately 90°, the feature amount (4) that can be calculated at the end of a meal tends to be larger than 90° and, as an example, be distributed to values such as 100° and 110°, and the feature amount (4) that can be calculated at the rest time tends to come close to 180°. Thus, the relation is: motion end time<meal end time<rest time. Therefore, as an example, it can be evaluated whether the candidate is plausible as the meal end time by setting an upper limit value of the feature amount (4) at the end of motion and a lower limit value of the feature amount (4) at the rest time, as boundary values and by checking whether it satisfies: upper limit value in the end of motion<feature amount (4)<lower limit value at the rest time.

[Feature Amount (5)]

Figure 8:
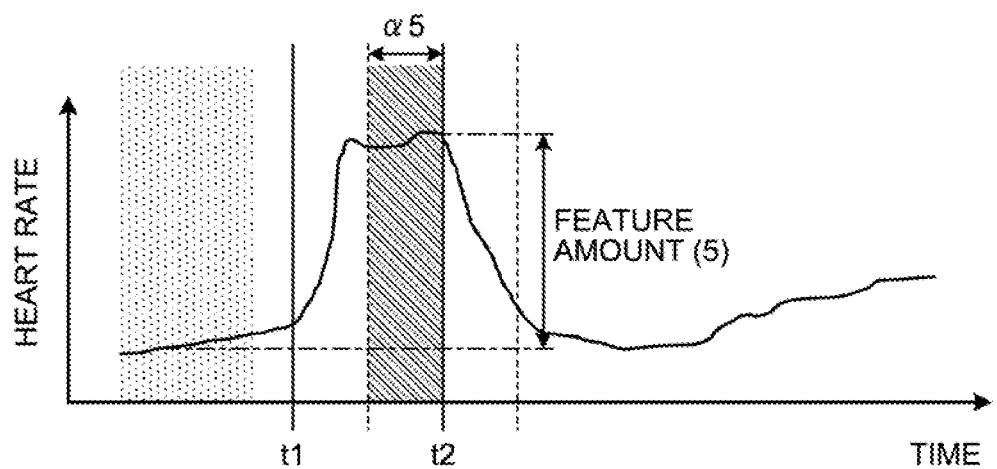
FIG. 8 is a diagram explaining an example of feature amount (5)

Next, the feature amount (5) will be described. The feature amount (5) is an index obtained by quantizing the difference between the heart rate during the meal (immediately before the end of a meal) and the heart rate before the start of a meal. FIG. 8 is a diagram explaining an example of the feature amount (5). FIG. 8 also illustrates, for convenience of explanation, a case where the candidate of the meal end time described above is set at a time point that the user inputs as the meal end in the heart rate data including the actual meal period. The vertical axis illustrated in FIG. 8 indicates the heart rate per unit time, and the horizontal axis indicates time. Note that "t1" illustrated in FIG. 8 indicates the meal start time and "t2" illustrated in FIG. 8 indicates the meal end time.

As illustrated in FIG. 8, the feature amount calculation unit 140, as an example, can calculate the difference between a first section from a predetermined time α5 before the meal end time t2 that is the candidate, that is, a center value in a dark filled section in the drawing, and a second section that is a time zone that can be assumed to be before the start of a meal, for example, from an hour before to 30 minutes before the meal end time t2 that is the candidate, that is a center value in a light filled section in the drawing, as the feature amount (5). As an example, a case is described where the difference between center values is determined. However, it is acceptable that any statistics such as an arithmetic mean, a weighted average, and a moving average is determined and the difference between the statistics is determined. In addition, as an example of the predetermined time α5, as similar to the α2 of the feature amount (2) described above, an extent of time, for example, three minutes or the like can be adopted in which it is assumed that, when the user eats a certain amount of food, eating action and peristaltic action continue. In a case of the feature amount (5) calculated in this way, relation among the feature amounts (5) that can be calculated at the rest time in which activities such as motion are not performed, at the actual meal end time, and at the motion end time is the relation: rest time<meal end time<motion end time. Therefore, as an example, it can be evaluated whether the candidate is plausible as the meal end time by setting an upper limit value of the feature amount (5) at the rest time and a lower limit value of the feature amount (5) at the end of motion, as boundary values and by checking whether it satisfies: upper limit value at the rest time<feature amount (5)<lower limit value in the end of motion. Note that, when the meal start time is known, a predetermined time in minutes (for example, 30 minutes) before that time may be regarded as the second section.

Note that, as an example of the calculation method of the feature amount (5), a case is described where the difference between the center value of the first section and the center value of the second section is calculated as the feature amount (5). However, the calculation method of the feature amount (5) is not limited to this. As another example, the feature amount calculation unit 140 may determine a difference between the heart rate measured at the meal end time t2 that is the candidate instead of the center value of the first section, and the center value of the second section to calculate the difference as the feature amount (5).

[Feature Amount (6)]

Next, the feature amount (6) will be described. The feature amount (6) is an index obtained by quantizing occurrence probability of the heart rate during the meal (immediately before the end of a meal) with respect to a set of the heart rates before the start of a meal. For example, the feature amount calculation unit 140 creates probability distribution of the heart rate included in the heart rate data of the second section that has been described with reference to FIG. 8. When the probability distribution is created in this way, the feature amount calculation unit 140 can create the probability distribution by imparting a larger weight to the heart rate of a time that is close to the meal end time t2 that is the candidate among the heart rates included in the second section, than the heart rate of a time that is further from the meal end time t2. In addition, the feature amount calculation unit 140 calculates the occurrence probability of the heart rate for every heart rate included in the heart rate data that corresponds to the first section, that is, the section during the meal, from the occurrence probability created beforehand from the second section, that is, the set of the heart rates of before the start of a meal. As a result, the feature amount calculation unit 140 derives the largest value in the occurrence probability calculated for every heart rate included in the first section, as the feature amount (6). Note that, although a case of using the largest value in the occurrence probability is described, a predetermined number of a higher level in the occurrence probability, for example, the occurrence probability of first place through tenth place, or the occurrence probability of upper ⅕ can be derived instead of the largest value, as the feature amount (6) in order to determine a feature amount that is robust for generation of noise and heart rate change.

Figure 9:
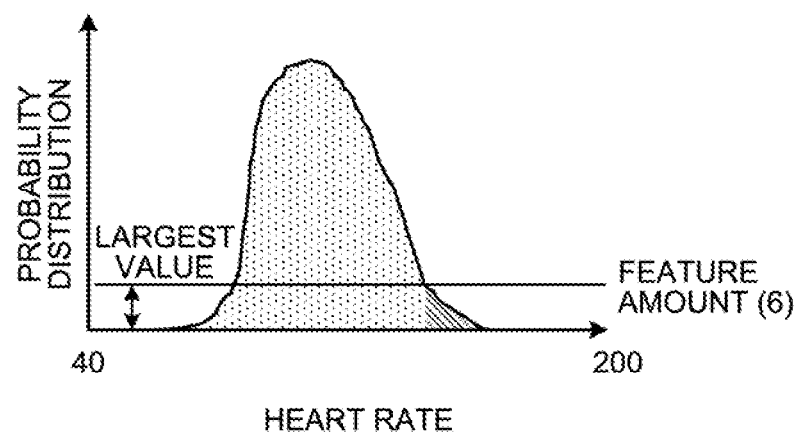
FIG. 9 is a diagram explaining an example of feature amount (6)

FIG. 9 is a diagram explaining an example of the feature amount (6). FIG. 9 illustrates the occurrence probability determined from the set of the heart rates included in the heart rate data of the second section illustrated in FIG. 8. The vertical axis illustrated in FIG. 9 indicates the probability or probability density, and the horizontal axis indicates the heart rate. As illustrated in FIG. 9, when the candidate is set to the actual meal end time from the feature (a) described above, the distribution of the heart rate in the first section, that is, the dark filled section, appears in the right side of the distribution of the heart rate in the second section, that is, the light filled section, that is, appears in the higher heart rate. Furthermore, the occurrence probability in the first section is, even though it is the largest value, smaller than the largest value of the occurrence probability of the heart rate included in the second section. According to such feature amount (6), it can be considered that, the smaller the value of the feature amount (6) is, the longer a state in which the heart rate during the meal is higher than that before the start of a meal, that is, a state in which the heart rate is higher than that at the rest time, continues. Thus, it can be evaluated that the partial data around the candidate of the meal end time described above is similar to the feature (a).

Note that, although, as an example of the calculation method of the feature amount (6), a case where the occurrence probability is created from the set of the heart rates included in the heart rate data in the second section is exemplified, the calculation method of the feature amount (6) is not limited to this. As another example, when the meal start time is known, the feature amount calculation unit 140 may create the occurrence probability from the set of the heart rates included in the heart rate data in the section from an hour before the meal end time t2 that is the candidate until the meal start time t1, instead of the second section, to calculate the feature amount (6).

[Feature Amount (7)]

Figure 10:
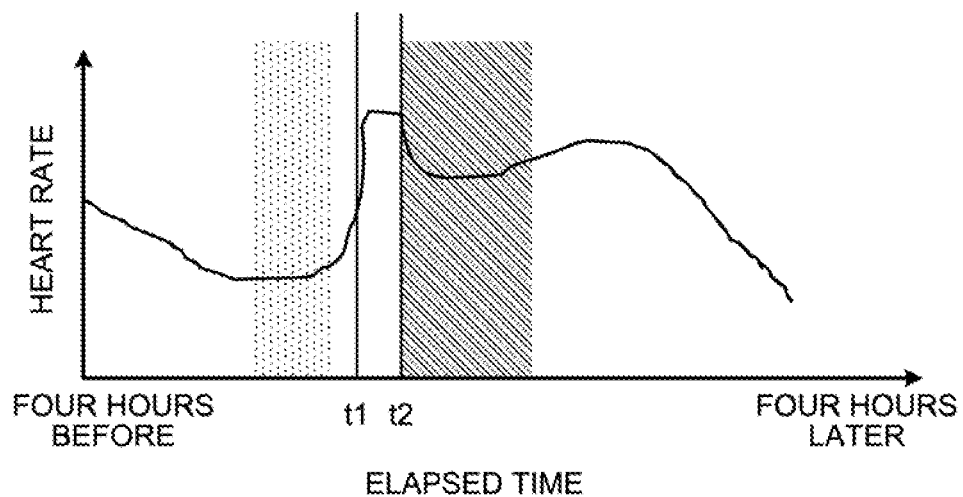
FIG. 10 is a diagram explaining an example of feature amount (7)
Figure 11:
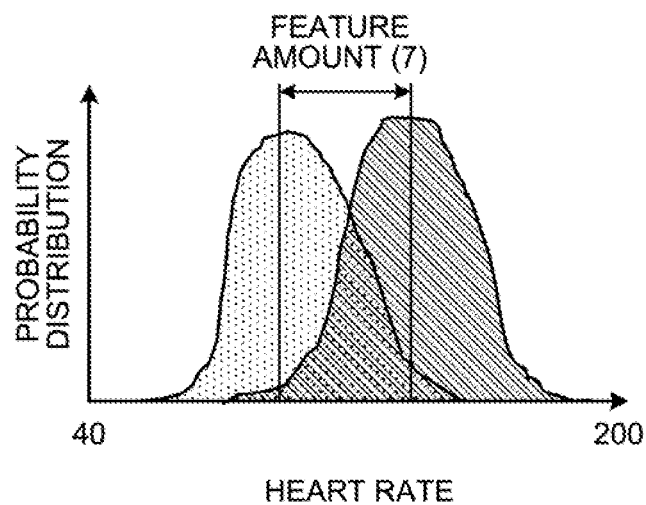
FIG. 11 is a diagram explaining an example of the feature amount (7)

Next, the feature amount (7) will be described. The feature amount (7) is an index obtained by quantizing the degree of similarity between the heart rate distribution after the end of a meal and the heart rate distribution before the start of a meal. FIG. 10 and FIG. 11 are diagrams explaining an example of the feature amount (7). FIG. 10 illustrates the heart rate data of from four hours before the meal end time t2 that is the candidate until four hours after the meal end time t2, and illustrates, for convenience of explanation, a case where the candidate of the meal end time described above is set at a time point that the user inputs as the meal end in the heart rate data including the actual meal period. The vertical axis illustrated in FIG. 10 indicates the heart rate per unit time, and the horizontal axis indicates time. Note that "t1" illustrated in FIG. 10 indicates the meal start time and "t2" illustrated in FIG. 10 indicates the meal end time.

As illustrated in FIG. 10, the feature amount calculation unit 140, as an example, creates the occurrence probability of the heart rate included in the heart rate data in the third section from the meal end time t2 that is the candidate until a predetermined time $\alpha 6$, that is, the dark filled section in the drawing. As an example of the predetermined time $\alpha 6$, when the candidate is set to the actual meal end time, an extent of time, for example, one hour or the like can be adopted in which the tendency of the feature (c) described above appears. Together with this, the feature amount calculation unit 140 creates the occurrence probability of the heart rate included in the heart rate data in the second section that has been described with reference to FIG. 8, that is, the light filled section in the drawing. As a result, as illustrated in FIG. 11, the occurrence probability in the third section and the occurrence probability in the second section are created. In addition, as illustrated in FIG. 11, the feature amount calculation unit 140 calculates the difference between the heart rate having the largest probability density in the probability distribution created from the third section, and the heart rate having the largest probability density in the probability distribution created from the second section, as the feature amount (7), and calculates the degree of similarity between the two probability distributions, for example, the inner product and the correlation coefficient as the feature amount (7). For example, when the degree of similarity of the inner product and the correlation coefficient is calculated as the feature amount (7), in the relation of the feature amounts (7) that can be calculated at the rest time in which activities such as motion are not performed, at the actual meal end time, at the actual meal end time, and at the end of motion, the feature amount (7) calculated at the meal end time is smaller than that calculated at any of the rest time and the motion end time. That is, the relation is: meal end time<rest time, and meal end time<motion end time. In this case, it can be evaluated whether the candidate is plausible as the meal end time by checking whether the feature amount (7) is lower than the lower limit value at the rest time and at the motion end time. In addition, when the difference of the heart rates that are the largest values is calculated as the feature amount (7), in the relation among the feature amounts (7) that can be calculated at the rest time in which activities such as motion are not performed, at the actual meal end time, and at the motion end time, the feature amount (7) calculated at the meal end time is larger than that calculated at any of the rest time and the motion end time.

That is, the relation is: meal end time>rest time, and meal end time>motion end time. In this case, it can be evaluated whether the candidate is plausible as the meal end time by checking whether the feature amount (7) is larger than the upper limit values at the rest time and at the motion end time. Note that any one of the degree of similarity described above and the difference between the heart rates that are the largest values can be calculated as the feature amount (7) and both of them can be calculated as the feature amount (7).

Note that, although, as an example of the calculation method of the feature amount (7), a case where the probability distribution is created from the set of the heart rate included in the heart rate data in the second section is exemplified, the calculation method of the feature amount (7) is not limited to this. As another example, when the meal start time is known, the feature amount calculation unit 140 may create the occurrence distribution from the set of the heart rates included in the heart rate data in the section from an hour before the meal end time t2 that is the candidate until the meal start time t1, instead of the second section, to calculate the feature amount (7).

As above, the feature amount calculation unit 140 can calculate at least any one feature amount of the seven feature amounts of the feature amount (1) to the feature amount (7) described above, or a combination of any number of the feature amounts, for each candidate described above.

For the description of FIG. 1 again, the meal time estimation unit 150 is a processing unit that estimates the meal time from the feature amount calculated by the feature amount calculation unit 140. The following exemplifies a case of using the feature amount (1), the feature amount (4), the feature amount (5), and the feature amount (6) for estimating the meal time, only as an example. However, other feature amounts may be used. The feature amount (1), the feature amount (4), the feature amount (5), and the feature amount (6) are not necessarily used for determining a threshold. In addition, as an example of the meal time, a case of estimating the meal end time is exemplified. However, the meal start time, the duration time for the meal, or the combination of these may be estimated.

The meal time estimation unit 150 illustrated in FIG. 1 has a determination unit 151, a grouping unit 152, and a decision unit 153.

Among these, the determination unit 151 is a processing unit that performs determination of comparing the feature amount calculated by the feature amount calculation unit 140 and a predetermined threshold.

As an embodiment, the determination unit 151 performs following processing each time the feature amount (1), the feature amount (4), the feature amount (5), and the feature amount (6) are calculated by the feature amount calculation unit 140. That is, the determination unit 151 determines whether the feature amount (1) is a predetermined threshold or more. Subsequently, when the feature amount (1) is the predetermined threshold or more, the determination unit 151 further determines whether the feature amount (5) is the predetermined threshold or less. Furthermore, when the feature amount (5) is the threshold or less, the determination unit 151 further determines whether the feature amount (6) is less than the predetermined threshold. As a result, when the feature amount (1) is the threshold or more, the feature amount (5) is the threshold or less, and the feature amount (6) is less than the threshold, it can be estimated that the candidate of the meal end time having these feature amount (1), feature amount (5), and feature amount (6) is plausible as the meal end time. In this case, the determination unit 151 records the candidate in an internal memory or the like (not illustrated), as the meal end time.

In the example described above, a case is exemplified where a classification tree for performing the threshold determination in order of the feature amount (1), the feature amount (5), and the feature amount (6), is used as a determination model. However, the determination model used for estimating the meal time is not limited to this. For example, any determination model can be generated by performing machine learning of training data with correct answers. That is, by deciding which feature amount among the seven feature amounts is used for threshold determination, and by deciding the order of the feature amounts for performing the threshold determination, the classification tree can be determined. Furthermore, by setting the magnitude of the threshold that is compared with the feature amount with the classification tree, or the like, the determination model can be generated. For example, the classification tree for performing the threshold determination for the feature amount other than the feature amount (1), the feature amount (5), and the feature amount (6) described above, that is, the feature amount (2), the feature amount (3), the feature amount (4), or the feature amount (7), can be generated.

By performing such machine learning, the following effect can be acquired. For example, in a case of the feature amount (1), it is considered that the most people have relation among the feature amounts (1) that can be calculated at the rest time in which activities such as motion are not performed, at the actual meal end time, and during the motion, being: rest time<meal end time<motion time. However, there are people who do not necessarily have the tendency of rest time<meal end time<motion time, of the feature amount (1). As an example, there are people having a tendency of rest time<motion time<meal end time, of the feature amount (1). Also in this case, by performing machine learning by using positive data and negative data of those people, the classification tree can be generated according to the tendency of the people.

The grouping unit 152 is a processing unit that groups the meal end times.

As an embodiment, the grouping unit 152 groups the meal end times having a time difference with each other that is within a predetermined period among the meal end times stored in the internal memory. For example, the grouping unit 152 applies identification information of the same group to each of the meal end times having a time difference with each other that is within the predetermined period, and applies identification information of different groups to the meal end times having a time difference with each other that is not within the predetermined period. In addition, the grouping unit 152 can implement the grouping described above by associating each of the meal end times with the identification information of the group applied to the end time and cause the associated times to be recorded in the internal memory.

The decision unit 153 is a processing unit that decides on one meal end time by using the meal end times grouped in the same group.

As an embodiment, the decision unit 153 selects the meal end time having the feature amount (4) calculated by the feature amount calculation unit 140 that is the lowest among the meal end times grouped in the same group by the grouping unit 152. Among the meal end times evaluated to be plausible based on the feature amount (1), the feature amount (5), and the feature amount (6), the meal end time that is further evaluated to be plausible based on the feature amount (4), can be extracted. Note that, although a case is exemplified where one meal end time is selected from among the meal end times grouped in the same group, predetermined statics, for example, the mean and the median, may be determined between the meal end times to decide the statics as the meal end time.

The service providing unit 160 is a processing unit that provides the health care supporting service described above.

As an embodiment, the service providing unit 160 records the meal time estimated by the meal time estimation unit 150, for example, at least one of the meal start time, the meal end time, or the duration time for a meal, generates a list of food time zones for a predetermined period, for example, for a week, from the meal time recoded by that time to output the list, and analyses for the eating habits or diet from the meal time recorded by that time to output various types of advice. Note that functions mounted in the service providing unit 160 may be implemented by an external server device, or the like.

Note that the function units such as the motion period determination unit 120, the noise heart rate removal unit 130, the feature amount calculation unit 140, the meal time estimation unit 150, and the service providing unit 160, described above can be mounted as follows. For example, the function units can be implemented by causing the central processing unit, what is called a CPU to expand the process that exhibits similar functions to the function units described above on the memory and execute the process. These function units are not necessarily performed in the central processing unit and may be performed by the MPU. In addition, the function units described above can be implemented also by the hardwired logic such as the ASIC and the FPGA.

Note that, in the main storage device used by the function units described above, as an example, various types of semiconductor memory elements, for example, the RAM or the flash memory can be adopted. In addition, the storage device referred to by the function units described above is not necessarily the main storage device and may be the auxiliary storage device. In this case, the HDD, the optical disc, or the SSD can be adopted.

[Processing Flow]

Figure 12:
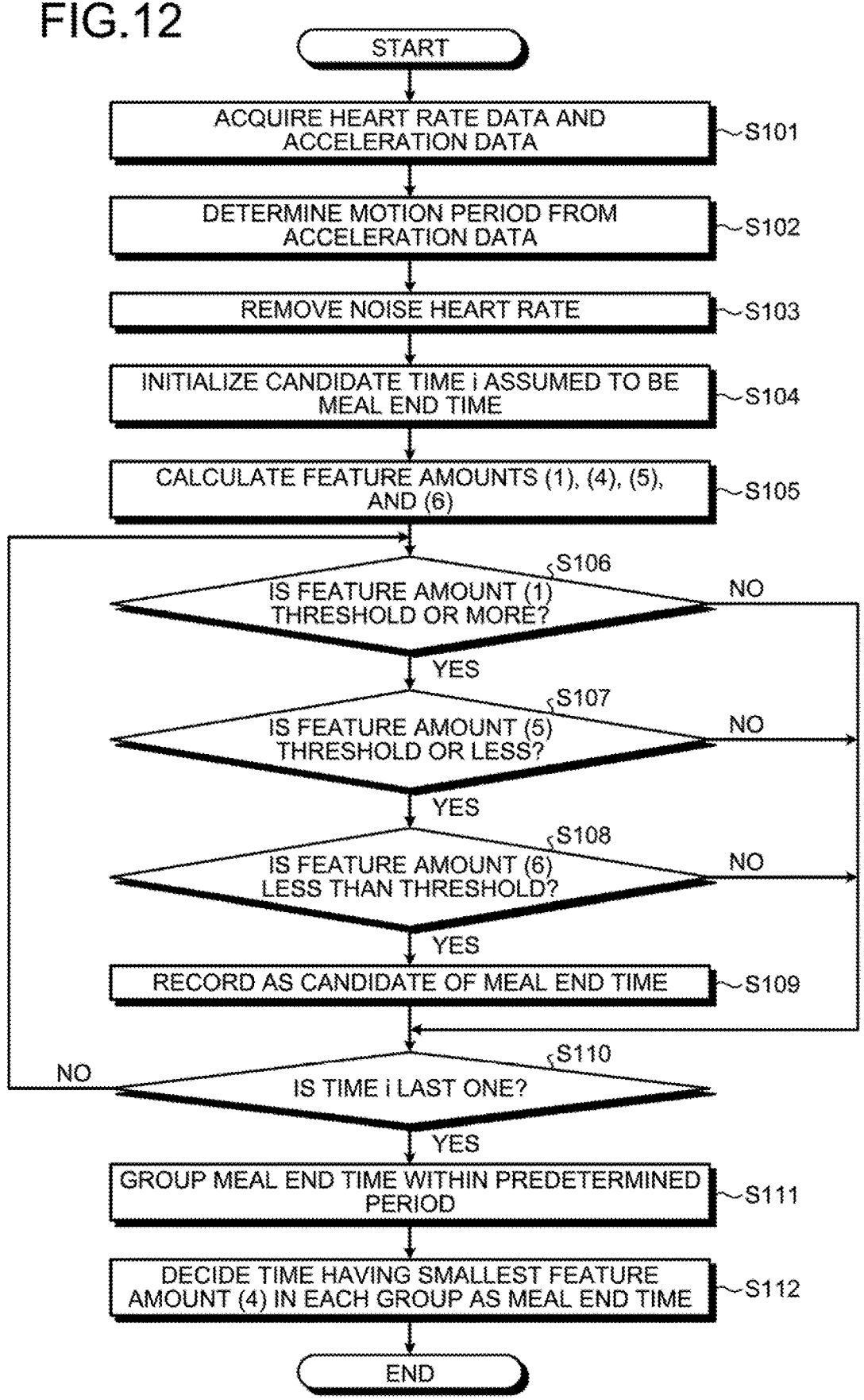
FIG. 12 is a flowchart illustrating a procedure of meal time estimation processing according to the first embodiment.

FIG. 12 is a flowchart illustrating a procedure of meal time estimation processing according to the first embodiment. As an example, this processing is activated when the heart rate data and the acceleration data for a predetermined time length, for example, 12 hours or a day is obtained.

As illustrated in FIG. 12, when the heart rate data and the acceleration data are acquired from the sensor terminal 10 (step S101), the motion period determination unit 120 performs following processing. That is, the motion period determination unit 120 uses the acceleration of the direction of gravitational force in the acceleration data acquired at step S101 to determine a section in which an interval of up and down patterns that correspond to the motion appears repeatedly in a predetermined period, as the motion period (step S102).

Subsequently, the noise heart rate removal unit 130 removes the section that corresponds to the removal period in which a certain period is added to the motion period determined at step S102, from the heart rate data acquired at step S101 (step S103).

Furthermore, the feature amount calculation unit 140 initializes a candidate time i assumed to be the meal end time on the heart rate data acquired at step S101 (step S104). For example, when the feature amount (1), the feature amount (4), the feature amount (5), and the feature amount (6) are calculated, data of until an hour before the candidate time i is used for estimating the meal time. Thus, the time that is an hour after the start time of the heart rate data acquired at step S101 is initialized as the candidate time i.

After that, the feature amount calculation unit 140 calculates the feature amount (1), the feature amount (4), the feature amount (5), and the feature amount (6) by using the heart rate data acquired at step S101 (step S105).

Subsequently, the determination unit 151 determines whether the feature amount (1) calculated at step S105 is a predetermined threshold or more (step S106). At this time, when the feature amount (1) is the threshold or more (Yes at S106), the determination unit 151 further determines whether the feature amount (5) is the predetermined threshold or less (step S107). Furthermore, when the feature amount (5) is the threshold or less (Yes at S107), the determination unit 151 further determines whether the feature amount (6) is less than the predetermined threshold (step S108).

When the feature amount (6) is less than the threshold (Yes at S108), it can be estimated that the candidate of the meal end time having these feature amount (1), feature amount (5), and feature amount (6), is plausible as the meal end time. In this case, the determination unit 151 records the candidate in an internal memory or the like (not illustrated), as the meal end time (step S109).

On the other hand, when the feature amount (1) is not the threshold or more, when the feature amount (5) is not the threshold or less, or when the feature amount (6) is not less than the threshold (No at S106, No at S107, or No at S108), it is estimated that the candidate of the meal end time is not plausible as the meal end time based on at least one of the feature amounts of the feature amount (1), the feature amount (5), and the feature amount (6). In this case, the candidate is not recorded as the meal end time.

Furthermore, when the last time in which the candidate time i can be incremented, for example, the feature amount (1), the feature amount (4), the feature amount (5), and the feature amount (6), is determined, the time i that is the candidate of the meal end time is incremented until the time is the predetermined time α1 (=α3) before the end time of the heart rate data acquired at step S101 (No at S110), and processing of step S106 through step S109 described above is performed repeatedly. The amount of increment of the candidate time i in this way may be in an arbitrary unit such as millisecond, second, and minute.

Furthermore, in the case where the last time, in which the candidate time i can be incremented, for example, the feature amount (1), the feature amount (4), the feature amount (5), and the feature amount (6), is determined, and when it is the time that is α1 (=α3) before the end time of the heart rate data acquired at step S101 (Yes at S110), the grouping unit 152 groups the meal end times having a time difference with each other that is within a predetermined period, among the meal end times recorded at step S109 (step S111).

After that, the decision unit 153 selects the meal end time having the lowest feature amount (4) calculated at step S105, from among the meal end times grouped in the same group at step S111 (step S112), and ends the processing.

[One Side of Effect]

As described above, the health care supporting system 1 according to the present embodiment uses the feature amounts that are obtained by indexing the degree of similarity with the feature of the heart rate change that appears at the end of the meal, is used when estimating the meal time such as the meal start time, the meal end time, and the duration time for a meal, from the time series data of the heart rate. This prevents the meal time from being estimated in a situation where the heart rate increases due to a factor other than the meal such as mental tension, change in environmental temperature, and exercises. Accordingly, the health care supporting system 1 according to the present embodiment can prevent the decrease of the estimation accuracy of the meal time.

Second Embodiment

Although the embodiment related to the disclosed device has been described, the present invention may be performed in various different modes other than the embodiment described above. Following describes other embodiments included in the present invention.

[Meal Start Time 1]

For the first embodiment described above, a case of estimating the meal end time has been exemplified. However, the meal start time can be estimated by using known algorithm. For example, the information processing device 100 refers to the heart rate data described above, and estimates the time at which a rise value of the heart rate becomes a threshold or more after a predetermined period, for example, three minutes later, as the meal start time, or estimates the time having the "positive" sign indicating inclination of the approximate line determined by the function approximation from the time series of the heart rate until after a predetermined period, and having the absolute value that is a predetermined threshold or more, as the meal start time.

[Meal Start Time 2]

Furthermore, the information processing device 100 can extract plausible meal start time from among the meal start times estimated as above, by using the meal end time estimated by the meal time estimation unit 150. For example, the information processing device 100 estimates the time that is before the meal end time estimated by the meal time estimation unit 150 among the meal start times estimated as above and is within a predetermined period, for example, an hour, from the meal end time, as the meal start time that is a pair with the meal end time estimated by the meal time estimation unit 150. Thereby, the plausible meal start time can be extracted by comparing with the meal end time estimated by the meal time estimation unit 150.

[Needed Time for Meal]

In the first embodiment described above, a case of estimating the meal end time has been exemplified. However, the duration time for a meal can be estimated by using known algorithm. For example, the information processing device 100 can calculate the duration time for a meal by calculating the difference between the meal end time estimated by the meal time estimation unit 150 and the meal start time estimated as above. In this case, the information processing device 100 can set the meal start times that are before the meal end time estimated by the meal time estimation unit 150 among the meal start times estimated as above, to the calculation target of the duration time for a meal, or can extract the duration time for a meal having a time length within a predetermined threshold, for example, an hour or an hour and a half.

Another First Embodiment

For the first embodiment described above, a case where a client server system including the sensor terminal 10 and the information processing device 100 is constituted has been exemplified. However, the present invention is not limited to this. For example, a series of processing from the acquisition of the heart rate data to the estimation of the meal time may be performed by the sensor terminal 10, the information processing device 100, or other computers, as a stand-alone device.

Another Second Embodiment

In addition, each of components of each of the device illustrated is not necessarily physically configured as illustrated. That is, particular forms of distribution or integration of each of devices are not limited to that illustrated. Whole or a part of those can be configured by functionally or physically distributing or integrating in an arbitrary unit according to various types of loads and the use state. For example, for the first embodiment described above, a case where the information processing device 100 performs the meal time estimation processing illustrated in FIG. 12 has been exemplified. However, the performing subject of the processing is not limited to this. For example, the information processing device 100 may function as a relay device that relays the heart rate data and the acceleration data from the sensor terminal 10 and may cause a cloud that provides the health care supporting service described above through a Web server or outsourcing that provides the health care supporting service described above to perform the meal time estimation processing described above.

[Meal Time Estimation Program]

In addition, various types of processing that have been described for embodiments described above can be implemented by executing a computer program prepared beforehand by a computer such as a personal computer and a workstation. The following describes an example of a computer that executes a meal time estimation program having a similar function to the embodiments described above, with reference to FIG. 13.

Figure 13:
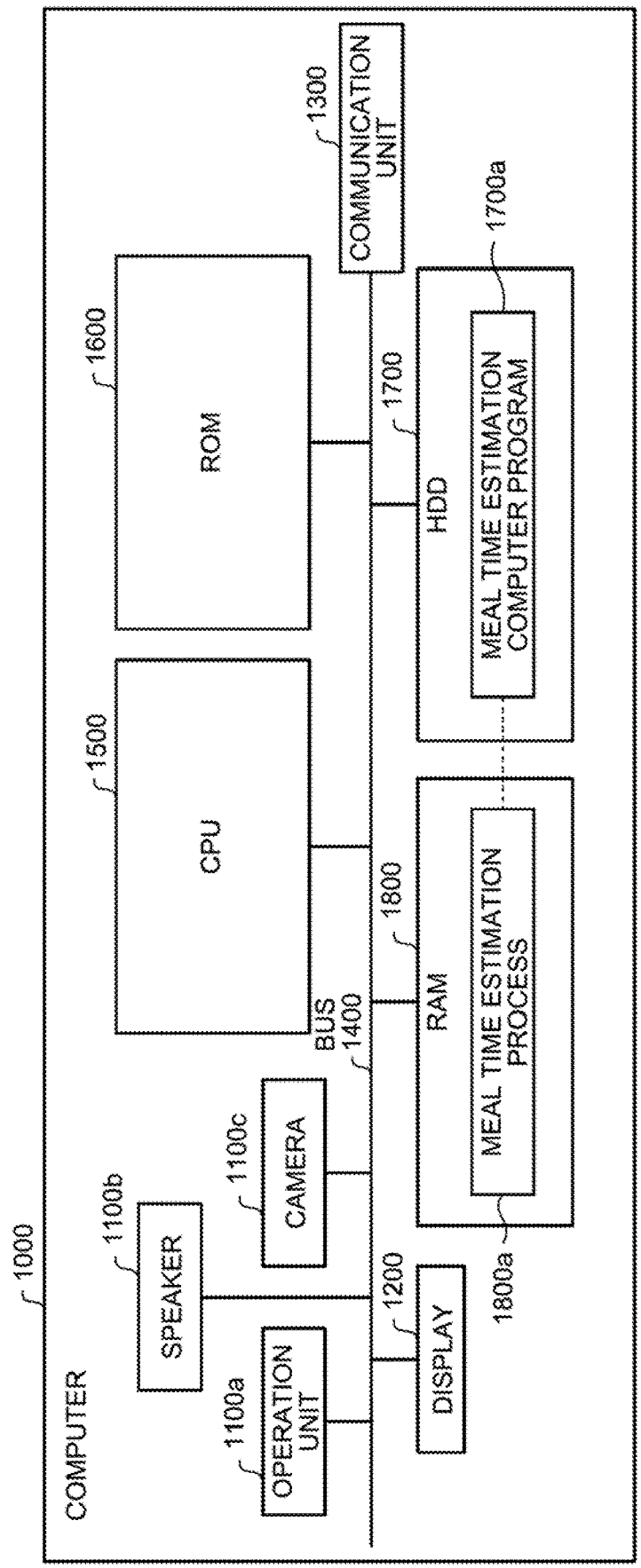
FIG. 13 is a diagram illustrating an example of configuration of hardware of a computer that executes a meal time estimation program according to the first embodiment and a second embodiment.

FIG. 13 is a diagram illustrating an example of configuration of hardware of a computer that executes the meal time estimation program according to the first embodiment and the second embodiment. As illustrated in FIG. 13, a computer 1000 has an operation unit 1100a, a speaker 1100b, a camera 1100c, a display 1200, and a communication unit 1300. Furthermore, the computer 1000 has a CPU 1500, a ROM 1600, a HDD 1700, and a RAM 1800. Each part of these 1100 to 1800 is connected via a bus 1400.

As illustrated in FIG. 13, in the HDD 1700, a meal time estimation program 1700a that exhibits similar functions to the motion period determination unit 120, the noise heart rate removal unit 130, the feature amount calculation unit 140, and the meal time estimation unit 150 that have been described for the first embodiment described above, is stored. The meal time estimation program 1700a may be integrated or separated as similar to each of the components of the motion period determination unit 120, the noise heart rate removal unit 130, the feature amount calculation unit 140, and the meal time estimation unit 150 illustrated in FIG. 1. That is, in the HDD 1700, all data described for the first embodiment described above is not necessarily stored and it is enough that data used for processing is stored in the HDD 1700.

Under such environment, the CPU 1500 reads out the meal time estimation program 1700a from the HDD 1700 and expands the meal time estimation program 1700a in the RAM 1800. As a result, as illustrated in FIG. 13, the meal time estimation program 1700a functions as meal time estimation process 1800a. The meal time estimation process 1800a expands various types of data read out from the HDD 1700 in a region assigned to the meal time estimation process 1800a among storage regions that the RAM 1800 has, and performs various types of processing by using the expanded various types of data. For example, examples of processing that the meal time estimation process 1800a performs include processing illustrated in FIG. 12. Note that, in the CPU 1500, all of the processing units described for the first embodiment described above do not necessarily operate and, it is enough that a processing unit that corresponds to processing to be performed, is performed virtually.

Note that the meal time estimation program 1700a described above is not necessarily stored in the HDD 1700 or the ROM 1600 from the start. For example, each computer program is stored in a "portable physical media" such as, a flexible disc, what is called a FD, a CD-ROM, a DVD disc, a magneto-optical disc, and an IC card that are inserted to the computer 1000. Then, the computer 1000 may acquire each computer program from the portable physical media and executes the computer program. In addition, each computer program is stored in other computer or server device connected to the computer 1000 via a public network, the Internet, a LAN, a WAN, or the like, and then the computer 1000 may acquire each program from the computer or the server device and execute the computer program.

The present invention can prevent a decrease in measurement accuracy of a meal time.

All examples and conditional language provided herein are intended for the pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A meal time estimation device comprising:
a memory; and
a processor coupled to the memory and configured to:
acquire time series data of heart rate,
calculate a feature amount obtained by indexing a degree of similarity with a feature of heart rate change that appears at end of a meal from the time series data of the heart rate by calculating, while shifting a candidate of a meal end time assumed to be the meal end time in the heart rate data, the feature amount by using partial data around the candidate in the heart rate data for every candidate, the indexing including indexing the degree that the partial data around the candidate of the meal end time is similar with the feature, as the feature amount, to evaluate whether the candidate is plausible as the meal end time, the feature of heart rate change being stored in the memory beforehand, and being the heart rate data including a meal period from a meal start to a meal end, and
estimate a meal time from the feature amount, which is hard to change by a factor other than the meal to prevent a decrease in estimation accuracy of the meal time by occurrence of erroneous determination,
wherein the estimate the meal time includes the processor being configured to
estimate the meal time from the feature amount by performing determination of comparing the feature amount calculated and a predetermined threshold, grouping the meal end times, the grouping includes grouping the meal end times having a time difference with each other that is within a predetermined period among the meal end times stored in the memory, select the meal end time having the lowest feature amount calculated, from among the meal end times grouped in the same group, estimate the meal end time from the feature amount, estimate a candidate that corresponds to the meal end time among candidates of meal start time extracted from the time series data of the heart rate, as the meal start time, when estimating the meal start time, and estimate a candidate having a period that is within a predetermined range, among candidates of the duration time for a meal determined from a set of the first candidate meal start time and the first candidate meal end time that correspond to each other, when estimating the duration time for a meal, as the duration time for a meal, the candidates of meal start time being the time that is before the estimated meal end time and that is within a predetermined period from the meal end time, and the candidates of the duration time being created by calculating a difference between the estimated meal end time and the candidates of meal start time, and estimate at least two of the meal end time, the meal start time, and the duration time for a meal.

2. A meal time estimation method comprising:

acquiring time series data of heart rate, by a processor;

calculating a feature amount obtained by indexing a degree of similarity with a feature of heart rate change that appears at end of a meal from the time series data of the heart rate, by the processor by calculating, while shifting a candidate of a meal end time assumed to be the meal end time in the heart rate data, the feature amount by using partial data around the candidate in the heart rate data for every candidate, the indexing including indexing the degree that the partial data around the candidate of the meal end time is similar with the feature, as the feature amount, to evaluate whether the candidate is plausible as the meal end time, the feature of heart rate change being stored in a memory beforehand, and being the heart rate data including a meal period from a meal start to a meal end; and estimating a meal time from the feature amount, which is hard to change by a factor other than the meal, by the processor, to prevent a decrease in estimation accuracy of the meal time by occurrence of erroneous determination, wherein the estimating includes estimating the meal time from the feature amount by performing determination of comparing the feature amount calculated and a predetermined threshold, grouping the meal end times, the grouping includes grouping the meal end times having a time difference with each other that is within a predetermined period among the meal end times stored in the memory, selecting the meal end time having the lowest feature amount calculated, from among the meal end times grouped in the same group, estimating the meal end time from the feature amount, estimating a candidate that corresponds to the meal end time among candidates of meal start time extracted from the time series data of the heart rate, as the meal start time, when estimating the meal start time, and estimating a candidate having a period that is within a predetermined range, among candidates of the duration time for a meal determined from a set of the first candidate meal start time and the first candidate meal end time that correspond to each other, when estimating the duration time for a meal, as the duration time for a meal, by the processor, the candidates of meal start time being the time that is before the estimated meal end time and that is within a predetermined period from the meal end time, and the candidates of the duration time being created by calculating a difference between the estimated meal end time and the candidates of meal start time, and estimating at least two of the meal end time, the meal start time, and the duration time for a meal.

3. The meal time estimation method according to claim 2, wherein the calculating includes calculating a feature amount obtained by quantifying inclination of the heart rate of immediately before the end of the meal associated with the feature, a feature amount obtained by quantifying inclination of the heart rate of immediately after the end of the meal, a feature amount obtained by quantifying an angle formed by a waveform of heart rate data of immediately before the end of the meal and immediately after the end of the meal, a feature amount obtained by quantifying a difference between the heart rate of during the meal or immediately before the end of the meal, and the heart rate of before the start of the meal, a feature amount obtained by quantifying occurrence probability of the heart rate of during the meal or immediately before the end of the meal with respect to a set of heart rates of before the start of the meal, or a feature amount obtained by quantifying a degree of similarity between heart rate distribution of after the end of the meal and heart rate distribution of before the start of the meal or any combination thereof, by the processor, and the estimating includes estimating the meal time from the feature amount by performing determination of comparing the feature amount calculated and a predetermined threshold, grouping the meal end times, and deciding on one meal end time by using the meal end times grouped in the same group, and preventing the meal time from being estimated in a situation where the heart rate increases due to a factor other than the meal.

4. The meal time estimation method according to claim 2, wherein the acquiring includes acquiring time series data of inertia, by the processor, and the meal time estimation method further includes:

determining amplitude change corresponding to motion from the time series data of inertia, by the processor; and removing a section of the amplitude change corresponding to the motion from the time series data of the heart rate, or interpolating the section after the removal, by the processor.

5. A non-transitory computer-readable recording medium storing a meal time estimation program that causes a computer to execute a process, the process comprising:

acquiring time series data of heart rate;

calculating a feature amount obtained by indexing a degree of similarity with a feature of heart rate change that appears at end of a meal from the time series data of the heart rate, by calculating, while shifting a candidate of a meal end time assumed to be the meal end time in the heart rate data, the feature amount by using partial data around the candidate in the heart rate data for every candidate, the indexing including indexing the degree that the partial data around the candidate of the meal end time is similar with the feature, as the feature amount, to evaluate whether the candidate is plausible as the meal end time, the feature of heart rate change being stored in a memory beforehand, and being the heart rate data including a meal period from a meal start to a meal end; and estimating a meal time from the feature amount, which is hard to change by a factor other than the meal to prevent a decrease in estimation accuracy of the meal time by occurrence of erroneous determination, wherein the estimating includes estimating the meal time from the feature amount by performing determination of comparing the feature amount calculated and a predetermined threshold, grouping the meal end times, the grouping includes grouping the meal end times having a time difference with each other that is within a predetermined period among the meal end times stored in the memory, selecting the meal end time having the lowest feature amount calculated, from among the meal end times grouped in the same group, estimating the meal end time from the feature amount, estimating a candidate that corresponds to the meal end time among candidates of meal start time extracted from the time series data of the heart rate, as the meal start time, when estimating the meal start time, and estimating a candidate having a period that is within a predetermined range, among candidates of the duration time for a meal determined from a set of the first candidate meal start time and the first candidate meal end time that correspond to each other, when estimating the duration time for a meal, as the duration time for a meal, the candidates of meal start time being the time that is before the estimated meal end time and that is within a predetermined period from the meal end time, and the candidates of the duration time being created by calculating a difference between the estimated meal end time and the candidates of meal start time, and estimating at least two of the meal end time, the meal start time, and the duration time for a meal.

6. The non-transitory computer-readable recording medium according to claim 5, wherein the calculating includes calculating a feature amount obtained by quantifying inclination of the heart rate of immediately before the end of the meal associated with the feature, a feature amount obtained by quantifying inclination of the heart rate of immediately after the end of the meal, a feature amount obtained by quantifying an angle formed by a waveform of heart rate data of immediately before the end of the meal and immediately after the end of the meal, a feature amount obtained by quantifying a difference between the heart rate of during the meal or immediately before the end of the meal, and the heart rate of before the start of the meal, a feature amount obtained by quantifying occurrence probability of the heart rate of during the meal or immediately before the end of the meal with respect to a set of heart rates of before the start of the meal, and a feature amount obtained by quantifying a degree of similarity between heart rate distribution of after the end of the meal and heart rate distribution of before the start of the meal or any combination thereof, and the estimating includes estimating the meal time from the feature amount by performing determination of comparing the feature amount calculated and a predetermined threshold, grouping the meal end times, and deciding on one meal end time by using the meal end times grouped in the same group, and preventing the meal time from being estimated in a situation where the heart rate increases due to a factor other than the meal.

7. The non-transitory computer-readable recording medium according to claim 5, wherein the acquiring includes acquiring time series data of inertia, the process further includes:

determining amplitude change corresponding to motion from the time series data of inertia; and removing a section of the amplitude change corresponding to the motion from the time series data of the heart rate, or interpolating the section after the removal.

* * * * *